(12) United States Patent
Dvorak et al.

(10) Patent No.: US 11,414,443 B2
(45) Date of Patent: Aug. 16, 2022

(54) PHOSPHOLIPID DERIVATIVES AND THEIR USE AS MEDICAMENTS

(71) Applicants: USTAV MOLEKULARNI GENETIKY AV CR, V.V.I., Prague (CZ); SMART BRAIN S.R.O., Prague (CZ)

(72) Inventors: Michal Dvorak, Prague (CZ); Marta Dvorakova, Prague (CZ); Vit Karafiat, Prague (CZ); Jan Stursa, Prague (CZ); Lukas Werner, Velke Popovice-Brtnice (CZ); Lucie Janeckova, Prague (CZ)

(73) Assignees: USTAV MOLEKULARNI GENETIKY AV CR, V.V.I., Prague (CZ); SMART BRAIN S.R.O., Prague (CZ)

(*) Notice: Subject to any disclaimer, the term of this patent is extended or adjusted under 35 U.S.C. 154(b) by 0 days.

(21) Appl. No.: 16/500,552

(22) PCT Filed: Mar. 29, 2018

(86) PCT No.: PCT/CZ2018/050015
§ 371 (c)(1),
(2) Date: Oct. 3, 2019

(87) PCT Pub. No.: WO2018/184604
PCT Pub. Date: Oct. 11, 2018

(65) Prior Publication Data
US 2020/0102333 A1  Apr. 2, 2020

(30) Foreign Application Priority Data
Apr. 3, 2017 (CZ) .................. CZ2017-190

(51) Int. Cl.
C07F 9/10 (2006.01)
A61P 35/00 (2006.01)
A61K 9/00 (2006.01)
A61K 31/704 (2006.01)

(52) U.S. Cl.
CPC .............. *C07F 9/10* (2013.01); *A61K 9/0019* (2013.01); *A61K 9/0053* (2013.01); *A61P 35/00* (2018.01); *A61K 31/704* (2013.01)

(58) Field of Classification Search
None
See application file for complete search history.

(56) References Cited

U.S. PATENT DOCUMENTS 4,372,949 A    2/1983  Kodama et al.
5,149,527 A *  9/1992  Weisenthal ............ A61K 35/74
                                                      424/85.2

FOREIGN PATENT DOCUMENTS

WO    WO-2007056264 A2 *  5/2007 ............ A61K 33/24

OTHER PUBLICATIONS

E. Gendaszewska-Darmach, "Lysophosphatidic acids, cyclic phosphatidic acids and autotaxin as promissing targets in therapies of cancer and other diseases", Acta Biochimica Polonica, 55(Feb. 2008), pp. 227-240 (2008).
M.G.K. Benesch, et al., "Autotaxin in the crosshairs: Taking aim at cancer and other inflammatory conditions", FEBS Letters, 588, pp. 2712-2727 (2014).
P. Abramowski, et al., "The Orally Available, Synthetic Ether Lipid Edelfosine Inhibits T Cell Proliferation and Induces a Type I Interferon Response", PLOS One, 9(3), pp. 1-15 (2014).
B.S. Mamatha, et al., "Effect of micellar lipids, dietary fiber and beta-carotene on lutein bioavailability in aged rats with lutein deficiency", Nutrition, 27, pp. 960-966 (2011).
M. Riederer, et al., "Acyl chain-dependent effect of lysophosphatidylcholine on endothelial prostacyclin production", Journal of Lipid Research, 51, pp. 2957-2966 (2010).
M.O.W. Grimm, et al., "From brain to food: Analysis of phosphatidylcholins, lyso-phosphatidylcholins and phosphatidylcholin-plasmalogens derivates in Alzheimer's disease human post mortem brains and mice model via mass spectrometry", Journal of Chromatography A, 1218, pp. 7713-7722 (2011).
M.C. Jin, et al., "Suppressive effect of docosahexaenoyl-lysophosphatidylcholine and 17-hydroxydocosahexaenoyl-lysophosphatidylcholine on levels of cytokines in spleen of mice treated with lipopolysaccharide", Eur. J. Lipid Sci. Technol., 114, pp. 114-122 (2012).
K. Yea, et al., "Lysophosphatidylcholine Activates Adipocyte Glucose Uptake and Lowers Blood Glucose Levels in Murine Models of Diabetes", The Journal of Biological Chemistry, 284(49), pp. 33833-33840 (2009).
H.A. Overton, et al., "GPR119, a novel G protein-coupled receptor target for the treatment of type 2 diabetes and obesity", British Journal of Pharmacology, 153, pp. S76-S81 (2008).
G.B. Mills, et al., "The Emerging Role of Lysophosphatidic Acid in Cancer", Nature, 3, pp. 582-591 (2003).
M. Gotoh, et al., "Controlling cancer through the autotaxin-lysophosphatidic acid receptor axis", Biochem. Soc. Trans., 40(1), pp. 31-36 (2012).

(Continued)

*Primary Examiner* — Joseph R Kosack
(74) *Attorney, Agent, or Firm* — Venable LLP

(57) ABSTRACT

The present invention relates to 1-acyl-lysophosphatidyl derivatives of general formula I;

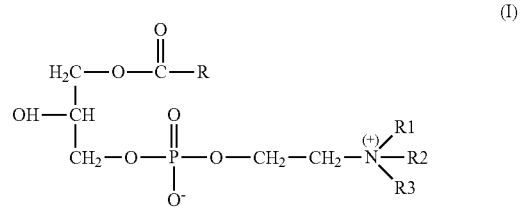

in which R is C4 to C30 aliphatic hydrocarbyl chain, R1 is selected from H or C1 to C10 alkyl, preferably C1 to C6 alkyl, R2 is selected from H, C10 to C30 acyl or C1 to C10 alkyl, preferably C1 to C6 alkyl, and R3, when present, is selected from H or C1 to C10 alkyl, preferably C1 to C6 alkyl. These derivatives are intended for the treatment of cancer, in particular melanoma, hepatocarcinoma or GIT carcinomas.

14 Claims, No Drawings

(56) References Cited

OTHER PUBLICATIONS

A.J.S. Houben, et al., "Autotaxin and LPA receptor signaling in cancer", Cancer Metastasis Rev., 30, pp. 557-565 (2011).
N. Niezgoda, et al., "Phosphatidylcholine with cis-9, trans-11 and trans-10, cis-12 Conjugated Linoleic Acid Isomers: Synthesis and Cytotoxic Studies", Aust J. Chem., 68, pp. 1065-1075 (2015).
A. Sowinska, et al., "The chemical synthesis and preliminary biological studies of phosphodiester and phosphorothioate analogues of 2-methoxy-lysophosphatidylethanolamine", Bioorganic & Medicinal Chemistry Letters, 26, pp. 3725-3729 (2016).
International Search Report and Written Opinion issued in corresponding international application No. PCT/CZ2018/050015 (13 pages).

\* cited by examiner

PHOSPHOLIPID DERIVATIVES AND THEIR USE AS MEDICAMENTS

FIELD OF ART

The present invention relate to lysophospholipid-based compounds, and to their use as medicaments.

BACKGROUND ART

Phospholipids are a key component of all biological membranes—they form the basis of the membrane bilayer together with proteins, glycolipids and cholesterol derivatives. They confer on the membranes their specific semi-permeable properties. Lipids from hen egg yolks contain a significant amount (20%) of phospholipids. Dominant phospholipids of the egg yolk are phosphatidylcholine (75%) and phosphatidylethanolamine (20% of all egg yolk phospholipids). Furthermore, the yolks contain small amounts of phosphatidylserine, phosphatidylinositol, phosphatidic acid, sphingomyelin and others in trace amounts.

Upon eating food, the lipids are emulsified in the intestine with bile salts, absorbed and processed by intestinal lining cells, enterocytes. The first step in the digestion of phospholipids is their cleavage with phospholipase A2, which is secreted by small intestine enterocytes, to form lysophospholipids and free fatty acids. These substances are then absorbed by enterocytes, metabolized and incorporated into lipoprotein particles (e.g., chylomicrons) which serve as vehicles for transporting these substances through the lymphatic system and bloodstream to the cells of other tissues.

Glycerol-based lysophospholipids occur in organisms not only as intermediates in the synthesis of various phospholipids, but, as has been shown recently, also have their own significant regulatory functions. There is hardly any information about the biological activity of 1-acyl lysophosphatidylcholine or of a mixture of 1-acyl lysophospholipids prepared from a natural mixture of phospholipids using phospholipase A2 and about their possible therapeutic use. It appears that 1-acyl lysoPC is indirectly involved in organ regeneration and wound healing (1, 2) and may possibly be used to treat autoimmune and degenerative diseases (3-7), and perhaps could be useful in the treatment of diabetes (8, 9). In blood serum, lysophosphatidylcholine is the most abundant lysophospholipid. It is a substrate for the enzyme autotaxin. In body fluids, autotaxin, which is a phospholipase D, cleaves choline group from lysophosphatidylcholine to form lysophosphatidic acid (LPA). LPA is a relatively well-studied substance due to its significant biological effects. LPA activates cell proliferation and angiogenesis and has pro-inflammatory and pro-tumor effects. Signaling pathways controlled by this acid through LPA receptors play a major role in carcinogenesis, tumor cell invasiveness and metastatic potential. The LPA signaling appears to be involved in the resistance of some types of cancer towards therapy (10-12).

Although it can be expected that 1-acyl lysophosphatidylcholine, due to its conversion to a pro-tumor LPA, will exhibit pro-tumor effects in vivo, we have found in the framework of the present invention that it inhibits the development of experimental liver tumors in chickens and subcutaneous and intraperitoneal tumors induced by syngeneic tumor cells in mice as well as the growth of spontaneous gastrointestinal tumors in APC/Min mice.

This surprising observation is the basis of the present invention.

Literature:
1. Gendaszewska-Darmach E.: Acta Biochim. Pol. 55, 227 (2008).
2. Benesch M. G., Ko Y. M., McMullen T. P., Brindley D. N.: FEBS Lett. (2014)
3. Abramowski P., Otto B., Martin R.: PLoS One 9, e91970 (2014).
4. Mamatha B. S., Baskaran. V.: Nutrition 27, 960 (2011)
5. Riederer M., Ojala P. J., Hrzenjak A., Graier W. F., Malli R., Tritscher M., Hermansson M. et al.: J. Lipid Res. 51, 2957 (2010).
6. Grimm M. O., Grosgen S., Reimenschneider M., Tanila H., Grimm H. S., Hartmann T.: J. Chromatogr A 1218, 7713 (2011).
7. Jin M. C., Hung N. D., Yoo J. M., Kim M. R., Sok D.: J. Lipid. Sci. Technol. 114, 114 (2012).
8. Yea K., Kim J., Yoon J. H., Kwon T., Kim J. H., Lee H. J, Kim J. I. et al.: J. Biol. Chem. 284, 33833 (2009).
9. Overton H. A., Fyfe M. C. T., Reynet C.: Br. J. Pharmacol. 153, 76 (2008).).
10. Mills G B, Moolenaar W H. The emerging role of lysophosphatidic acid in cancer. Nat Rev Cancer. 2003; 3(8):582-91.
11. Mari Gotoh a ost. Controlling cancer through the autotaxin-lysophosphatidic acid receptor axis. Biochem Soc Trans. 2012 February; 40(1): 31-36. doi:10.1042/BST20110608.
12. Houben A J, Moolenaar W H. Autotaxin and LPA receptor signaling in cancer. Cancer Metastasis Rev. 2011; 30(3-4):557-65.).

DISCLOSURE OF THE INVENTION

The present invention relates to 1-acyl-lysophosphatidyl derivatives of general formula I,

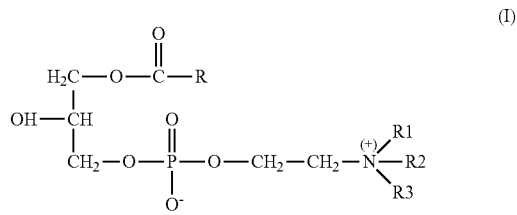

wherein
R is C4 to C30 alifatic hydrocarbyl chain,
R1 is selected from H or C1 to C10 alkyl, preferably C1 to C6 alkyl,
R2 is selected from H, C10 to C30 acyl or C1 to C10 alkyl (preferably C1 to C6 alkyl),
R3 is selected from H or C1 to C10 alkyl, preferably C1 to C6 alkyl, or R3 is not present.

Preferably R is selected from the group consisting of C5 to C10 linear, branched or cyclic or cycle-containing alkyl or alkenyl, such as pentyl or 3,5,5-trimethylpentyl, cyclopentylethyl; or C13 to C30, preferably C13 to C20 linear or branched alkyl or alkenyl, in particular C15, C16, C17, C18 or C19 linear alkyl or alkenyl. Alkenyls contain one or more double bonds.

Preferably, R2 is selected from the group consisting of C10-C30, preferably C10-C20 acyls containing linear saturated or unsaturated chains, such as decanoyl, palmitoyl, stearoyl, oleoyl, linoleoyl, elaidoyl.

When a molecule or a part thereof carries an electric charge, the charge is compensated for by a counterion.

Suitable counterions include alkali metal cations, halogen anions, or anions derived from inorganic or organic acids. Alternatively the charge can be compensated for by formation of an internal salt—betaine.

The nitrogen atom carries a positive charge when R3 is present.

In one preferred embodiment, at least one of R1, R2, R3 is methyl. In one particular embodiment, R1, R2 and R3 are methyls.

In one particular embodiment, R1 and R2 are H, and R3 is not present.

In one particular embodiment, R1 is H and R2 is C10-C20 acyl containing linear saturated or unsaturated chains, and R3 is not present.

The compounds of the present invention show cytotoxic effects on tumor cells, thus suppressing the growth of tumor cells. The object of the present invention are therefore the compounds of general formula (I) for use as medicaments, especially for the treatment of cancer, more particularly for the treatment of solid tumors. Solid tumors are in particular selected from gastrointestinal tract (GIT) carcinoma, melanoma and hepatocarcinoma. It has been shown within the framework of the present invention that the compounds of the general formula (I) are potent inhibitors of the growth of various tumor cells in tissue culture as well as inhibitors of the growth of experimental tumors in animal models.

The compounds of formula (I) may be prepared by selective deacylation of the respective phospholipids, optionally modified phospholipids. Starting phospholipids may include phosphatidylcholines, phosphatidylethanolamines, their derivatives by substitution on a nitrogen atom, or natural mixtures of phospholipids, optionally modified by substitution on a nitrogen atom. Natural mixtures of phospholipids may include, for example, egg yolk phospholipids. Selective deacylation can be accomplished by synthetic procedures known to those skilled in the art or enzymatically.

After selective deacylation, a subsequent acylation can also be performed to provide a compound carrying the desired acyl radical R. The acylation carried out after deacylation must be selective—this can be achieved, for example, by protecting the —OH group by protecting groups well known to those skilled in the art.

The compound of formula I can be isolated after deacylation from the reaction mixture either alone or in admixture with the free fatty acid. The presence of fa acid does not influence the cytotoxic effects of the compounds of formula I.

The object of the present invention is furthermore a pharmaceutical composition comprising at least one compound of general formula (I) and at least one carrier, diluent or filler. The pharmaceutical composition may further contain other suitable auxiliaries such as lubricants, tabletting-facilitating agents, emulsifiers, coatings, etc. The pharmaceutical composition may be in the form, for example, of capsules, tablets, ointments, creams, suspensions, emulsions, solutions. It may be preferably in a form destined for oral or intravenous administration.

A further object of the present invention is at least one 1-acyl-lysophosphatidyl derivative of general formula (I) for use in a method of treatment of cancer, wherein further an anticancer drug is administered. Preferably, the cancer is a solid tumor, preferably a hepatocarcinoma, a gastrointestinal tract carcinoma or a melanoma. Preferably, the anticancer drug is doxorubicin. Within the framework of the present invention, it was found that 1-acyl-lysophosphatidyl derivatives show an effect of synergistically potentiating the effects of the established anticancer drugs. The co-administration of the 1-acyl-lysophosphatidyl derivative of formula (I) with an anticancer drug leads to dose reduction of the anticancer drug and thereby to increasing efficacy while decreasing the toxicity of the drug and the unwanted side effects of the anticancer drugs. The co-administration of the 1-acyl-lysophosphatidyl derivative of formula (I) with an anticancer drug is preferably performed in the ratio of at least 20:1, preferably at least 50:1, more preferably at least 100:1, even more preferably at least 180:1 or at least 200:1. The substances can be administered together or within 12 hours of each other, preferably within 6 hours of each other, more preferably 2 hours of each other.

EXAMPLES OF CARRYING OUT THE INVENTION

Abbreviations:
PC—phosphatidylcholine
PE—phosphatidylethanolamine
E-DAPL—mixture of 1-acyl-lysophospholipids from egg yolk, obtained using phospholipase A2
TLC—thin-layer chromatography
FA—fatty acids
DMAP—dimethylaminopyridine
DCC—N,N'-dicyclohexylcarbodiimide Example 1

Isolation of Naturally Occurring Mixture of Phospholipids from Egg Yolks 20 egg yolks were mixed for 10 minutes at 30° C. with 1200 ml of 96% ethanol containing 0.01 mM 2,6-bis(1,1-dimethylethyl)-4-methylphenol. The mixture was filtered through a Whatman 1 filter paper and the filtrate was evaporated on a rotary vacuum evaporator. The residue was dissolved in 200 ml of n-hexane (25° C.) and the insoluble fraction was removed by centrifugation for 10 minutes at 3000×g, 25° C. The clear supernatant was cooled to 4° C., mixed with 2 volumes of acetone (4° C.) and left overnight at 4° C. The precipitate was washed three times with n-hexane:acetone (1:2) and dried in a desiccator under reduced pressure. The thus purified phospholipids were used either to isolate phosphatidylcholine and phosphatidylethanolamine or to prepare a mixture of lysophospholipids. The phospholipid content was determined by measuring the amount of phosphorus.

Example 2

Isolation of Phosphatidylcholine (PC) and Phosphatidylethanolamine (PE)

Purified total phospholipids (1.2 g) were dissolved in a small volume of chloroform:methanol:water (66:33:2) mixture and loaded onto a 100 ml silica gel column equilibrated in the same solvent mixture. The column was eluted with the same solvent mixture. A sample from each fraction was analyzed by TLC.

The combined fractions containing either PE or PC were evaporated and used to prepare 1-acyl-lysophosphatidylethanolamine (1-acyl-lysoPE), 1-acyl lysophosphatidylcholine (1-acyl-lysoPC) and N-acyl-lysophosphatidylethanolamines Small aliquots of the combined PE and PC fractions were analyzed using MALDI-TOF, NMR and TLC along with the standards. These methods verified that the fractions contain practically only PE or PC.

Structural analysis of phosphatidylcholine (PC) indicated palmitic and oleic acid diesters as the major component and minor esters with a set of naturally occurring fatty acids.

MS calculated: 760.5851; found: 760.5853 (M+)

IR: 3384 (m), 3007 (m), 2853 (m), 1738 (s), 1602 (s), 1467 (m), 1419 (m), 1378 (m), 1346 (m), 1249 (s), 1174 (m), 1092 (s), 1064 (s), 969 (s), 925 (s), 874 (s), 821 (m), 761 (m), 721 (s), 579 (m), 506 (m), 461 (m)cm$^{-1}$ $^1$H NMR (500 MHz, Methanol-d4) δ 5.35 (t, J=5.2 Hz, 4H), 5.25 (d, J=3.8 Hz, 1H), 4.44 (dd, J=12.0, 3.1 Hz, 1H), 4.32-4.23 (m, 2H), 4.17 (dd, J=12.0, 6.9 Hz, 1H), 4.00 (t, J=6.1 Hz, 2H), 3.68-3.60 (m, 2H), 3.23 (s, 9H), 2.33 (dt, J=14.3, 7.4 Hz, 4H), 2.11-1.94 (m, 4H), 1.67-1.50 (m, 4H), 1.46-1.23 (m, 44H), 0.99-0.82 (m, 6H).

$^{13}$C NMR (126 MHz, Methanol-d4) δ 173.49, 173.15, 129.44 (d, J=20.1 Hz), 127.69 (d, J=14.5 Hz), 70.40 (d, J=7.9 Hz), 66.08 (dd, J=7.2, 3.4 Hz), 63.47 (d, J=5.1 Hz), 62.30, 59.07 (d, J=4.9 Hz), 53.33, 53.30, 53.27, 33.70, 33.55, 31.69, 29.47, 29.42, 29.28, 29.24, 29.08, 28.99, 28.88, 28.85, 28.80, 26.79, 24.63, 22.36, 13.09.

Minori Signals:

$^1$H NMR (500 MHz, Methanol-d4) δ 3.61 (d, J=6.9 Hz), 3.35 (s), 2.89-2.72 (m), 2.40 (d, J=3.2 Hz), 2.14 (d, J=6.7 Hz), 1.74-1.65 (m), 1.18 (t, J=7.0 Hz), 0.98 (t, J=7.5 Hz).

$^{13}$C NMR (126 MHz, Methanol-d4) δ 172.97, 172.49, 129.82, 129.56, 129.43, 128.93, 128.58, 128.09, 127.82, 127.43 (d, J=16.2 Hz), 70.51, 48.45, 33.09, 31.29, 26.15, 25.20 (d, J=3.0 Hz), 24.54, 22.26.

Structural analysis of phosphatidylethanolamine (PE) indicated palmitic and oleic acid diesters as the major component and minor esters with a set of naturally occurring fatty acids.

IR: 3374 (m), 2956 (m), 2925 (s), 2854 (m), 1741 (s), 1653 (m), 1490 (m), 1467 (m), 1457 (m), 1378 (m), 1227 (s), 1051 (m), 722 (m) cm$^{-1}$ $^1$H NMR (500 MHz, Methanol-d$_4$) δ 5.43-5.31 (m, 5H), 5.23 (d, J=3.4 Hz, 1H), 4.58 (s, 1H, NH2), 4.44 (dd, J=12.0, 3.2 Hz, 1H), 4.24-4.14 (m, 1H), 4.04 (dd, J=5.2, 2.7 Hz, 2H), 4.02-3.97 (m, 2H), 3.16 (t, J=4.9 Hz, 2H), 2.92-2.78 (m, 4H), 2.33 (dt, J=12.9, 8.5 Hz, 4H), 2.11-2.00 (m, 4H), 1.65-1.57 (m, 4H), 1.38-1.24 (m, 38H), 0.95-0.86 (m, 6H).

Minor Signals:

$^1$H NMR (500 MHz, Methanol-d$_4$) δ 5.18-5.14 (m), 3.67-3.58 (m), 3.50-3.43 (m), 3.35 (s), 3.23 (s), 2.78 (t, J=6.7 Hz), 2.40 (d, J=3.9 Hz), 2.17-2.11 (m), 1.69 (td, J=7.3, 4.4 Hz), 0.98 (t, J=7.6 Hz).

Discrimination between signals for the major component (PE) and other components of the mixture was not possible. All signals are listed.

$^{13}$C NMR (126 MHz, Methanol-d$_4$) δ 174.94, 174.59, 174.39, 131.22, 130.96, 130.84 (d, J=19.8 Hz), 130.84, 130.34, 130.03-129.94 (m), 129.48, 129.27, 129.22, 129.17, 129.15, 129.10, 129.06-129.03 (m), 128.93, 128.84 (d, J=16.2 Hz), 72.03-72.00 (m), 71.95-71.91 (m), 71.89-71.84 (m), 71.79, 65.03-64.76 (m), 63.82-63.52 (m), 63.21-62.76 (m), 41.69 (d, J=6.3 Hz), 35.10, 34.93, 34.49, 33.09, 32.69, 30.86, 30.80, 30.64, 30.49, 30.47, 30.38, 30.26, 30.23, 30.20, 28.23, 28.17, 27.55, 26.61, 26.03, 25.93, 23.75, 14.46.

Example 3

Preparation of 1-acyl-lysophosphatidylethanolamine (1-acyl-lysoPE)

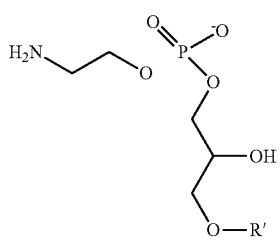

R' = acyl mixture, major component is palmitoyl

PE purified by flash chromatography or PE purchased from Sigma Aldrich at 10% (w/v) concentration were repeatedly vortexed and sonicated at 43° C. in 50 mM Tris-HCl (pH 8.0, 50 mM KCl, 8 mM CaCl$_2$) until the phospholipids were completely dispersed. The phospholipids were then digested with phospholipase A2 (EC 3.1.1.4) at a ratio of 2 units of enzyme/mg phospholipid at 43° C. and the reaction was monitored by silica gel thin layer chromatography (TLC), eluted with chloroform:methanol:water 20:10:1. After complete cleavage, the reaction was stopped by the addition of EDTA to a concentration of 10 mM and stored at 0-4° C. The resulting product was labeled PE/E-DAPL+FA (enzyme-digested 1-acyl-lysophosphatidylethanolamine in a mixture with fatty acids). Natural phosphatidylethanolamine typically carries the residue of palmitic acid, oleic acid or stearic acid as an acyl.

Example 4

Preparation of 1-acyl-lysophosphatidylcholine (1-acyl-lysoPC)

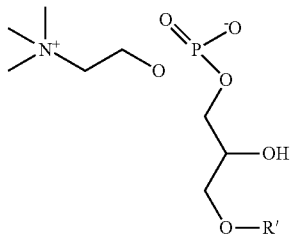

R' = acyl mixture, major component is palmitoyl

PC purified by flash chromatography at 10% (w/v) concentration was repeatedly vortexed and sonicated at 43° C. in 50 mM Tris-HCl (pH 8.0, 50 mM KCl, 8 mM CaCl$_2$) until the phospholipids were completely dispergated. PC was then digested with phospholipase A2 at a ratio of 2 units of enzyme/mg phospholipid at 43° C. and the reaction was monitored by silica gel thin layer chromatography (TLC), eluted with chloroform:methanol:water 20:10:1. After complete cleavage, the reaction was stopped by the addition of EDTA to a concentration of 10 mM and stored at 0-4° C. The resulting product was labeled PC/E-DAPL+FA (enzyme-digested 1-acyl-lysophosphatidylcholine in a mixture with fatty acids). Natural phosphatidylcholine typically carries the residue of palmitic acid, oleic acid or stearic acid as an acyl.

Example 5

Preparation of a Mixture of 1-acyl-lysophospholipids

Method A: Total purified phospholipids of Example 1 at 10% (w/v) concentration were repeatedly vortexed and sonicated at 43° C. in 50 mM Tris.HCl, pH 8.0, 50 mM KCl, 8 mM CaCl$_2$ until the phospholipids were perfectly dispergated. The phospholipids were then digested with phospholipase A2 at a ratio of 2 units of enzyme/mg phospholipid at 43° C. and the reaction was monitored by TLC, eluted with 20:10:1 chloroform:methanol:water mixture. After complete cleavage, the reaction was stopped by the addition of EDTA to a concentration of 10 mM and stored for a short time at 0-4° C. Method B: Dried total purified phospholipids of Example 1 were repeatedly vortexed and sonicated at 43° C. in 83 mM sodium deoxycholate in 50 mM Tris.Cl, pH 8.0, 50 mM KCl, 8 mM $CaCl_2$. The final concentration of phospholipids was also 83 mM (relative to PC). Phospholipids were then digested with phospholipase A2 at a rate of 0.2 units of enzyme/mg phospholipids at 43° C., and the reaction was monitored by TLC eluted with 20:10:1 chloroform:methanol:water mixture. After 120 minutes, the reaction was stopped by the addition of EDTA to a concentration of 10 mM, the pH of the mixture was adjusted to pH=3 with 1M HCl, the precipitated deoxycholic acid was removed by centrifugation and the supernatant was neutralized with 5M NaOH to pH=7. The reaction mixture was stored for a short time at 0-4° C. Products obtained by methods A and B were designated E-DAPL+FA.

The mixture E-DAPL+FA contains in particular 1-acyl-lysoPC and 1-acyl-lysoPE, which can be characterized by the formulas shown below, wherein R is mostly palmitic acid. The mixture also contains the fatty acid released from the enzymatic cleavage, mostly oleic acid.

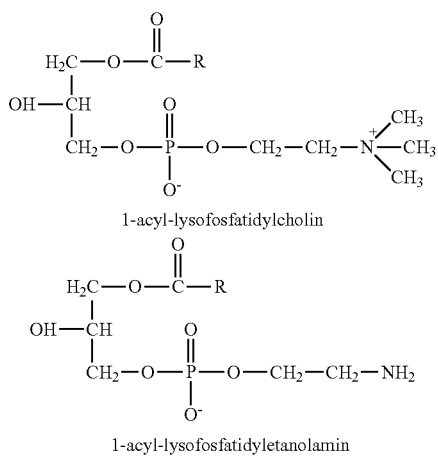

1-acyl-lysofosfatidylcholin 1-acyl-lysofosfatidyletanolamin

The spectrum of the purified 1-acyl-lysophosphatidylcholine:

$^1$H NMR (600 MHz, Methanol-$d_4$) δ 5.44-5.32 (m, 2H), 4.40-4.26 (m, 2H), 4.23-4.11 (m, 2H), 4.03-3.96 (m, 1H), 3.98-3.87 (m, 2H), 3.69-3.65 (m, 2H), 3.25 (s, 9H), 2.44-2.33 (m, 2H), 2.15-2.00 (m, 2H), 1.70-1.59 (m, 2H), 1.45-1.27 (m, 20H), 0.98-0.89 (m, 3H).

$^{13}$C NMR (151 MHz, Methanol-$d_4$) δ 175.71-175.03 (m), 130.83 (d, J=15.5 Hz), 129.07 (d, J=9.9 Hz), 69.84 (d, J=7.6 Hz), 67.85, 67.81, 67.49 (dd, J=6.9, 3.4 Hz), 66.24, 60.43 (d, J=5.1 Hz), 54.69 (d, J=7.6 Hz), 34.90, 33.05, 30.83, 30.81, 30.60, 30.43, 30.33, 30.31, 30.21, 30.20, 28.14 (d, J=5.2 Hz), 26.00 (d, J=5.3 Hz), 23.73, 14.45.

Minor Signals:

$^1$H NMR (600 MHz, Methanol-$d_4$) δ 5.05-4.98 (m), 4.07-4.02 (m), 3.80 (dd, J=5.7, 4.5 Hz), 3.75-3.70 (m), 3.65-3.56 (m), 3.37 (d, J=1.5 Hz), 3.13 (s), 2.91-2.83 (m), 2.82-2.78 (m), 2.44 (dd, J=5.6, 3.9 Hz), 2.34 (t, J=7.4 Hz), 2.20-2.14 (m), 2.13-2.08 (m), 1.75-1.68 (m), 1.00 (t, J=7.6 Hz).

$^{13}$C NMR (151 MHz, Methanol-$d_4$) δ 175.14, 175.09, 174.94, 131.19, 130.93, 130.85, 130.27, 130.01, 129.90, 129.45, 129.16 (d, J=1.5 Hz), 128.89, 128.76, 79.20 (d, J=6.1 Hz), 75.77 (d, J=5.8 Hz), 74.69 (d, J=8.1 Hz), 72.48 (d, J=7.5 Hz), 66.34, 64.73 (d, J=5.4 Hz), 64.55 (d, J=5.0 Hz), 63.78, 63.46 (d, J=4.5 Hz), 63.02 (d, J=4.2 Hz), 35.10, 34.81, 34.31, 32.66, 30.75, 30.71, 30.47, 30.17, 30.13, 27.55, 26.59-26.50 (m), 26.02, 25.89, 23.62

Example 6

Preparation of 2-acyl-lysophosphatidylcholine

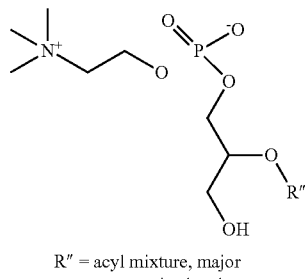

R″ = acyl mixture, major component is oleoyl

From the phosphatidylcholine isolated by the procedure of Example 2, the residue of the fatty acid in the sn-1 position was enzymatically removed. The PC in 10% (w/v) concentration was repeatedly vortexed and sonicated at 43° C. in 50 mM Tris.HCl, pH 8.0, 50 mM KCl, 8 mM $CaCl_2$ until it was completely dispergated. The PC was then digested with phospholipase A1 in a ratio of 2 enzyme units/mg of phospholipids at 37° C., and the reaction was monitored by TLC, eluted with 20:10:1 chloroform:methanol:water mixture. After the complete cleavage, EDTA was added to a concentration of 10 mM and the mixture was stored for a short time at 0-4° C. $^1$H NMR analysis of the product indicated 15-20% migration of acyl from sn-1 to give 1-acyl-lysophosphatidylcholine as a minor byproduct (see Example 5).

The Spectrum of 2-acyl-lysophosphatidylcholine:

$^1$H NMR (500 MHz, Methanol-d4) δ 5.42-5.27 (m, 2H), 5.05-4.97 (m, 1H), 4.35-4.22 (m, 2H), 4.01 (p, 2H), 3.75-3.68 (m, 2H), 3.66 (dd, J=5.5, 3.4 Hz, 2H), 3.24 (s, 9H), 2.83 (m, 1H), 2.37 (t, J=8.6, 6.5 Hz, 2H), 2.10-1.99 (m, 2H), 1.63 (t, J=7.2 Hz, 2H), 1.41-1.24 (m, 18H), 0.92 (t, J=6.9, 3.5 Hz, 2H).

$^{13}$C NMR (126 MHz, Methanol-d4) δ 174.95, 130.83 (d, J=12.1 Hz), 74.68 (d, J=8.5 Hz), 64.73 (d, J=5.5 Hz), 61.24, 60.42 (d, J=5.3 Hz), 54.72, 54.69, 54.66, 35.09, 30.83, 30.60, 30.44, 30.33, 30.21, 28.13, 25.97, 23.73, 14.46.

Minor Signals:

$^1$H NMR (500 MHz, Methanol-d4) δ 7.91 (s), 4.58 (s), 4.22-4.08 (m), 3.91 (q, J=6.3, 5.6 Hz), 3.77 (d, J=14.4 Hz), 3.36 (s), 3.09 (s), 2.94-2.73 (m), 2.24-2.09 (m), 1.71 (s), 1.19 (t, J=7.0 Hz), 0.99 (t, J=7.6 Hz). $^{13}$C NMR (126 MHz, Methanol-d4) δ 175.33, 131.20, 130.93, 130.25 (d, J=4.6 Hz), 129.96 (d, J=18.2 Hz), 129.46, 129.17, 128.83 (d, J=16.1 Hz), 73.34 (d, J=84.0 Hz), 70.87, 69.82 (d, J=7.7 Hz), 67.82 (d, J=5.7 Hz), 67.48 (dt, J=6.8, 3.2 Hz), 66.23, 64.73 (d, J=5.5 Hz), 64.14, 61.53, 34.90, 33.06, 30.83, 30.78, 30.47, 30.44, 26.55.

Example 7

Preparation of 1-acyl-specific 1,2-diacylphospholipids

From the phosphatidylcholine isolated according to Example 2, the sn-1 fatty acid residue of Example 6 was enzymatically removed, which was replaced by the acyl radical R' (see table below) with an organic esterification reaction.

The starting 2-acyl-lysophosphatidylcholine from Example 6 (1 eq) was dissolved in dry dichloromethane (0.06 M), the solution was cooled to 4° C., and the appropriate fatty acid (hexanoic, stearic, trimethylhexanoic, cyclopentanepropionic) chloride (3 eq). The reaction mixture was further heated to 10° C. and then pyridine (5 eq) and a catalytic amount of DMAP (0.05 eq) were slowly added dropwise. The mixture was stirred overnight at room temperature. The course of the reaction was monitored by TLC (CHCl$_3$/MeOH/H$_2$O in a ratio of 75/22.5/2.5). The reaction was quenched by extracting the reaction mixture in 50% aqueous NaCl and dichloromethane. The final product was obtained by column chromatography on silica gel (20% (MeOH+10% H$_2$O) in chloroform, +1% per minute). The resulting product is contaminated with the acylation product of 1-acyl-lysophosphatidylcholine (15-20%) resulting from the transacylation mechanism as a by-product of Example 6.

Example 8

Preparation of 1-hexanoyl-phosphatidylcholine

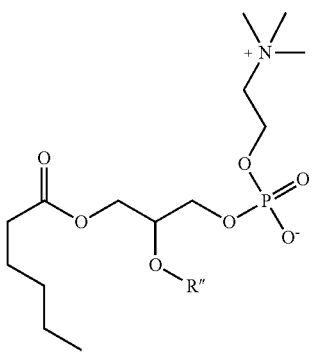

R" = acyl mixture, major component is oleoyl 1-hexanoyl-phosphatidylcholine was prepared by the procedure described in Example 7, in the yield of 43%.
MS: calculated: 619.4213; found: 619.4215

IR: 3373 (m), 3004 (w), 2925 (s), 2855 (m), 1737 (s), 1490 (sh), 1467 (m), 1380 (m), 1246 (s), 1051 (m), 928 (m), 726 (w) cm$^{-1}$ $^1$H NMR (600 MHz, Methanol-d$_4$) δ 5.44-5.32 (m, 2H), 5.32-5.24 (m, 1H), 4.46 (dd, J=12.1, 3.1 Hz, 1H), 4.36 (dd, J=6.5, 3.4 Hz, 2H), 4.21 (dd, J=12.1, 7.0 Hz, 1H), 4.06 (t, J=6.0 Hz, 2H), 3.82-3.68 (m, 2H), 3.30 (s, 9H), 2.36 (dt, J=15.1, 7.4 Hz, 4H), 2.16-1.97 (m, 4H), 1.64 (t, J=7.4 Hz, 4H), 1.42-1.26 (m, 22H), 0.98-0.88 (m, 6H).

$^{13}$C NMR (151 MHz, Methanol-d$_4$) δ 174.93, 174.62, 130.81 (d, J=27.4 Hz), 129.07 (d, J=18.3 Hz), 71.81 (d), 67.55-67.22 (m), 65.03 (d, J=4.5 Hz), 63.70, 60.70 (d, J=4.9 Hz), 54.79, 54.76, 54.74, 34.96 (d, J=33.0 Hz), 33.03, 32.39, 30.81, 30.72, 30.57, 30.45, 30.42, 30.33, 30.31, 30.29, 30.22, 30.21, 30.18, 30.16, 30.14, 28.12, 26.57, 26.54, 25.83 (d, J=52.5 Hz), 23.55 (d, J=47.9 Hz), 14.37 (d, J=23.1 Hz).

Minor Signals:

$^1$H NMR (600 MHz, Methanol-d$_4$) δ 5.16 (d, J=3.7 Hz), 4.63-4.57 (m), 4.52 (d, J=7.8 Hz), 4.32-4.28 (m), 3.88 (dd, J=11.9, 1.6 Hz), 3.83-3.79 (m), 3.71 (s), 2.92-2.83 (m), 2.80 (t, J=6.7 Hz), 2.16 (t, J=6.4 Hz), 1.76-1.70 (m), 1.48-1.44 (m), 1.11-0.98 (m).

$^{13}$C NMR (151 MHz, Methanol-d4) δ 131.20, 130.93, 130.80, 130.37, 129.95 (d, J=14.7 Hz), 129.47, 129.21, 128.80 (d, J=18.3 Hz), 98.15, 93.89, 77.99, 76.25, 74.83, 73.75, 72.97, 64.07, 62.73 (d, J=17.4 Hz), 60.99, 35.04, 34.88, 34.48, 32.65, 32.36, 30.81, 30.72, 30.57, 30.45, 30.42, 30.33, 30.31, 30.29, 30.22, 30.21, 30.18, 30.16, 30.14, 28.15, 27.50, 25.96, 25.69, 23.61, 14.37 (d, J=23.1 Hz).

Example 9

Preparation of 1-stearoyl-phosphatidylcholine

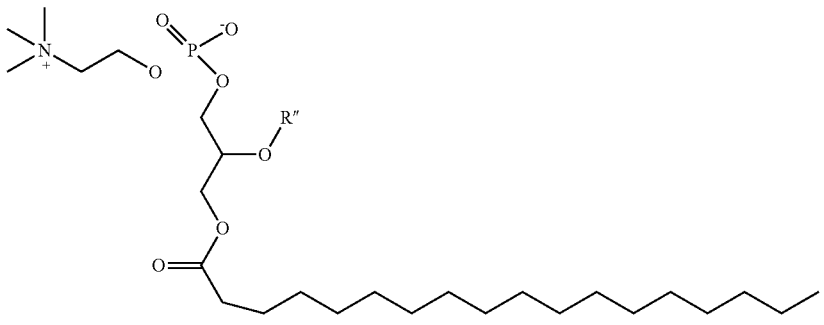

R" = acyl mixture, major component is oleoyl 1-stearoyl-phosphatidylcholine was prepared by the procedure described in Example 7, in the yield of 54%.
MS: calculated: 810.5983; found: 810,5989 (M+Na$^+$)

IR: 3408 (m), 30012 (w), 2957 (m), 2925 (s), 2852 (m), 1737 (s), 1490 (m), 1488 (sh), 1467 (m), 1378 (m), 1251 (s), 1063 (m), 926 (m), 721 (m) cm$^1$ $^1$H NMR (600 MHz, Methanol-d$_4$) δ 5.43-5.31 (m, 2H), 5.27-5.23 (m, 1H), 4.44 (dd, J=12.1, 3.0 Hz, 1H), 4.29 (t, J=4.6 Hz, 2H), 4.18 (dd, J=12.0, 7.0 Hz, 1H), 4.01 (t, J=6.0 Hz, 2H), 3.72-3.63 (m, 2H), 3.24 (s, 9H), 2.33 (dt, J=16.4, 7.4 Hz, 4H), 2.11-1.96 (m, 4H), 1.65-1.55 (m, 4H), 1.42-1.17 (m, 24H), 0.97-0.81 (m, 6H).

$^{13}$C NMR (151 MHz, Methanol-d$_4$) δ 175.01, 174.66, 130.84 (d, J=25.4 Hz), 129.08 (d, J=18.5 Hz), 71.83 (d, J=8.1 Hz), 67.46 (dt, J=7.1, 3.1 Hz), 64.90 (d, J=5.2 Hz), 63.73, 60.53 (d, J=5.0 Hz), 54.79, 54.76, 54.74, 35.04 (d, J=23.6 Hz), 33.06, 30.85, 30.83, 30.74, 30.64, 30.61, 30.46, 30.37, 30.35, 30.25, 30.21, 30.18, 28.50-27.96 (m), 26.03 (d, J=3.3 Hz), 23.73, 14.46.

Minor Signals:

$^1$H NMR (600 MHz, Methanol-d$_4$) δ 4.56 (s), 3.79 (s), 3.35 (s), 2.95-2.72 (m), 2.45-2.39 (m), 2.16 (s), 2.13 (t, J=6.9 Hz), 1.76-1.67 (m), 1.06-0.95 (m).

$^{13}$C NMR (151 MHz, Methanol-d$_4$) δ 174.97, 174.70, 136.28 (d, J=3.0 Hz), 134.77 (d, J=10.0 Hz), 131.53 (d, J=12.6 Hz), 131.22, 129.97 (d, J=5.1 Hz), 129.48, 129.31, 129.22, 128.88, 128.75, 108.23, 72.47, 64.12 (d, J=5.0 Hz), 34.51, 32.67, 30.45, 27.53, 26.59 (d, J=4.4 Hz), 25.93, 23.63, 14.48.

Example 10

Preparation of
1-trimethylhexanoyl-phosphatidylcholine

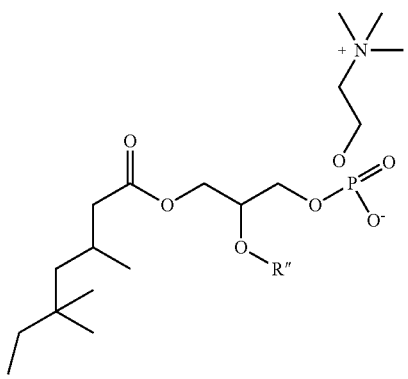

R″ = acyl mixture, major component is oleoyl 1-trimethylhexanoyl-phosphatidylcholine was prepared by the procedure described in Example 7, in the yield of 82%.

MS: calculated: 662.4755; found: 662.4758 (M+)

IR: 3404 (m), 3009 (w), 2957 (m), 2927 (s), 2855 (m), 1739 (s), 1478 (s), 1467 (m), 1394 (m), 1365 (m), 1247 (s), 1054 (m), 925 (m), 723 (m) cm$^{-1}$ $^1$H NMR (600 MHz, Methanol-d$_4$) δ 5.46-5.32 (m, 2H), 5.31-5.20 (m, 2H), 4.58 (s, 1H), 4.46 (ddd, J=22.6, 12.1, 3.2 Hz, 1H), 4.29 (tp, J=5.5, 2.7 Hz, 2H), 4.19 (ddd, J=21.8, 12.1, 6.9 Hz, 1H), 4.08-3.95 (m, 2H), 3.73-3.61 (m, 2H), 3.25 (s, 9H), 2.41-2.31 (m, 4H), 2.13-1.98 (m, 4H), 1.64 (dq, J=12.3, 7.4 Hz, 2H), 1.49-1.29 (m, 20H), 1.27 (d, J=4.2 Hz, 2H), 1.15 (ddd, J=14.0, 6.2, 1.9 Hz, 1H), 1.00 (d, J=6.6 Hz, 3H), 0.97-0.85 (m, 12H).

$^{13}$C NMR (151 MHz, Methanol-d$_4$) δ 174.58, 174.21, 130.84 (d, J=23.7 Hz), 129.18 (d, J=11.0 Hz), 71.84 (d, J=8.0 Hz), 67.48 (dt, J=6.8, 3.1 Hz), 65.14-64.30 (m), 63.70 (d, J=2.3 Hz), 60.47 (d, J=5.0 Hz), 55.06-54.34 (m), 51.64 (d, J=3.0 Hz), 49.85, 44.63 (d, J=1.5 Hz), 35.10, 33.06, 31.88, 30.83, 30.60, 30.45, 30.43, 30.34, 30.33, 30.22, 30.17, 28.16, 28.15, 26.56, 26.00 (d, J=1.3 Hz), 23.74, 23.15, 23.12, 14.47.

Minor Signals:

$^1$H NMR (600 MHz, Methanol-d$_4$) δ 5.47-5.36 (m), 2.93-2.82 (m), 2.80 (t, J=6.7 Hz), 2.22-2.11 (m), 1.72 (td, J=7.3, 3.8 Hz), 1.16 (dd, J=6.2, 1.9 Hz).

$^{13}$C NMR (151 MHz, Methanol-d$_4$) δ 131.22, 130.96, 130.84, 130.36, 129.99, 129.95, 129.93, 129.48, 129.14, 128.89, 128.77, 126.31, 34.51, 32.67, 30.73, 30.47, 30.24, 28.14, 26.60 (t, J=0.9 Hz), 25.92, 23.72, 23.63, 21.49.

Example 11

Preparation of
1-cyclopentanepropionyl-phosphatidylcholine

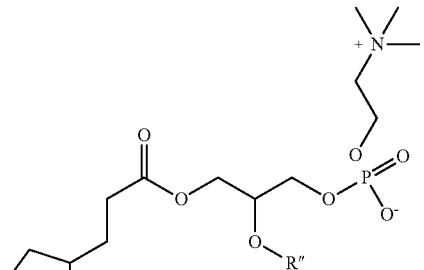

R″ = acyl mixture, major component is oleoyl 1-cyclopentanepropionyl-phosphatidylcholine was prepared by the procedure described in Example 7, in the yield of 71%.

MS: calculated: 668.4262; found: 668.4267 (M+Na$^+$)

IR: 3363 (m), 3008 (w), 2950 (sh), 2927 (s), 2856 (m), 1734 (s), 1487 (m), 1465 (m), 1553 (m), 1377 (m), 1245 (s), 1068 (m), 926 (m) cm$^{-1}$ $^1$H NMR (500 MHz, Methanol-d$_4$) δ 5.47-5.32 (m, 2H), 5.32-5.23 (m, 1H), 4.70-4.62 (m, 1H), 4.46 (dd, J=12.0, 3.2 Hz, 1H), 4.31 (tq, J=7.3, 2.6 Hz, 2H), 4.03 (t, J=5.9 Hz, 2H), 3.72-3.64 (m, 2H), 3.26 (s, 9H), 2.36 (td, J=7.6, 4.4 Hz, 4H), 2.18-2.04 (m, 4H), 1.81 (pd, J=6.7, 4.5, 3.8 Hz, 1H), 1.64 (q, J=5.8, 4.1 Hz, 4H), 1.56 (dp, J=7.1, 3.2 Hz, 4H), 1.45-1.28 (m, 20H), 1.22-1.07 (m, 4H), 0.93 (td, J=6.9, 3.4 Hz, 3H).

$^{13}$C NMR (126 MHz, Methanol-d$_4$) δ 130.82 (d, J=20.1 Hz), 129.35 (d, J=7.6 Hz), 77.92, 76.62, 75.61, 74.56, 74.38, 71.76, 69.56, 64.89 (d, J=5.2 Hz), 63.71, 61.86-60.10 (m), 57.72-53.49 (m), 35.08, 34.26, 33.43, 33.05, 32.24, 30.83, 30.59, 30.44, 30.34, 30.22, 30.16, 28.17, 26.10, 26.02, 23.73, 14.48.

Minor Signals:

$^1$H NMR (500 MHz, Methanol-d$_4$) δ 4.94 (dd, J=6.2, 2.8 Hz, 1H), 4.79 (d, J=11.4 Hz, 1H), 4.60-4.52 (m, 4H), 4.26-4.15 (m, 3H), 3.87-3.80 (m, 2H), 3.75 (dd, J=10.8, 2.9 Hz, 1H), 2.93-2.74 (m, 3H).

$^{13}$C NMR (126 MHz, Methanol-d$_4$) δ 139.75, 139.66, 139.39, 128.97 (d, J=3.6 Hz), 128.86-128.58 (m), 101.07, 40.87, 34.48, 32.66, 30.73, 30.46, 26.58, 23.62.

Example 12

Preparation of 1-palmitoyl-phosphatidylcholine

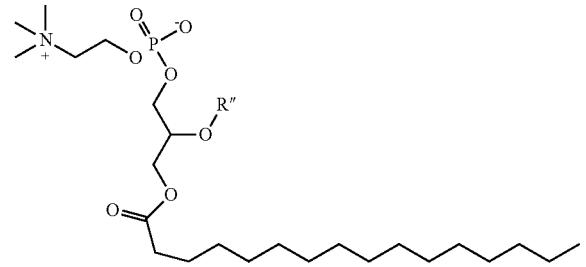

R″ = acyl mixture, major component is oleoyl 1-palmitoyl-phosphatidylcholine was prepared by the procedure described in Example 7, in the yield of 15%.

MS: calculated: 760.5851; found: 760.5855 (M+)

IR: 3403 (m), 3007 (w), 2956 (m), 2923 (s), 2853 (m), 1738 (s), 1478 (sh), 1467 (m), 1379 (m), 1251 (s), 1068 (m), 926 (m), 721 (m) cm$^{-1}$ $^1$H NMR (600 MHz, Methanol-d$_4$) δ 5.38 (td, J=4.9, 4.1, 1.2 Hz, 2H), 5.28 (dtd, J=6.9, 5.4, 3.1 Hz, 1H), 4.47 (dd, J=12.0, 3.2 Hz, 1H), 4.35-4.27 (m, 2H), 4.21 (dd, J=12.0, 6.9 Hz, 1H), 4.03 (ddd, J=6.7, 5.3, 1.3 Hz, 2H), 3.75-3.58 (m, 2H), 3.26 (s, 9H), 2.36 (dt, J=16.0, 7.4 Hz, 4H), 2.15-2.00 (m, 4H), 1.64 (pd, J=9.1, 8.0, 4.1 Hz, 4H), 1.46-1.24 (m, 44H), 0.93 (td, J=7.1, 1.4 Hz, 6H).

$^{13}$C NMR (151 MHz, Methanol-d$_4$) δ 174.90, 174.56, 130.84 (d, J=24.7 Hz), 71.81 (d, J=8.1 Hz), 67.49 (t, J=6.7 Hz), 64.90, 64.87, 63.69, 60.47 (d, J=5.0 Hz), 55.70-53.83 (m), 30.87, 30.82, 30.79, 30.67, 30.47, 30.38 (d, J=1.4 Hz), 30.27, 30.24, 30.20, 28.18, 26.05, 26.03, 23.75, 14.46.

1-acyl-specific 1,2-diacylphospholipids shown in examples 8-12 were digested by phospholipase A2 and purified as described in Example 4. This process yielded the following products which were designated as shown in the following table:

| R' | Designation |
|---|---|
| hexanoyl | sn-1 hexanoyl PC/E-DAPL + FA |
| stearoyl | sn-1 stearoyl PC/E-DAPL + FA |
| trimethylhexanoyl | sn-1 trimethylhexanoyl PC/E-DAPL + FA |
| cyclopentanepropionyl | sn-1 cyclopentanepropionyl PC/E-DAPL + FA |
| palmitoyl | sn-1 palmitoyl PC/E-DAPL + FA |

The products contained free (released) fatty acids (+FA) and major components were lysophospholipids having the following structures:

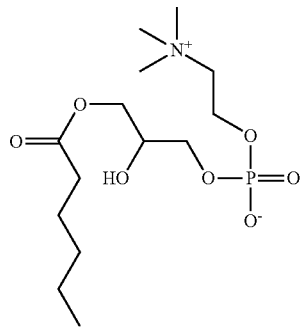

sn-1 hexanoyl PC/E-DAPL

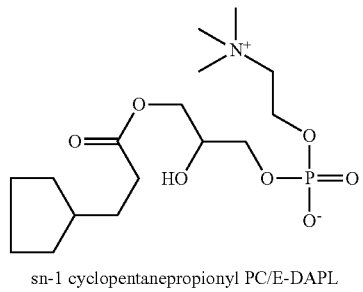

sn-1 cyclopentanepropionyl PC/E-DAPL

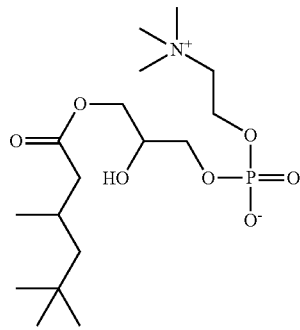

sn-1 trimethylhexanoyl PC/E-DAPL

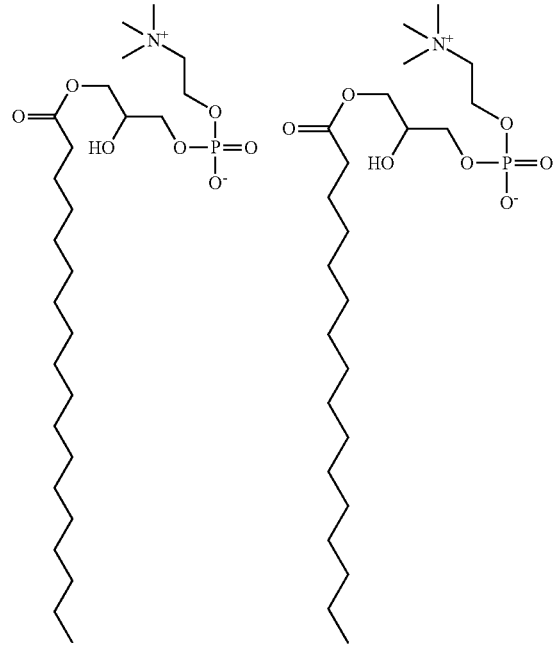

sn-1 stearoyl PC/E-DAPL     sn-1 palmitoyl PC/E-DAPL

Example 13

Preparation of N-acyl Derivatives of 1,2-diacyl-phosphatidylethanolamine

In the phosphatidylethanolamine isolated according to Example 2, the amino group hydrogen was replaced by the acyl radical R2 (see table below) using an esterification reaction. Phosphatidylethanolamine isolated from the natural source according to Example 2 carries in the sn-1 position a mixture of fatty acid residues, about 80% being palmitic acid residues, the rest being residues of stearic acid, oleic acid, and a small amount of other fatty acid residues.

Purified phosphatidylethanolamine was dissolved in anhydrous benzene and mixed with two equivalents of anhydride (palmitic, decanoic, oleic, linoleic or elaidic, respectively) in the presence of DMAP. The anhydrides were prepared by condensation of the relevant acids in the presence of DCC.

The N-acylation was carried out for 30 minutes at room temperature. The reaction mixture was dried, dissolved in hexane, the insoluble fraction was removed by centrifugation, and the N-acyl phosphatidylethanolamines were isolated by precipitation by 2 volume equivalents of acetone at 4° C. overnight. The precipitate was washed 3 times with ice cold hexane:acetone 1:2 at 0° C.

| R2 | Designation of the product |
| --- | --- |
| palmitoyl | N-palmitoyl PE |
| decanoyl | N-decanoyl PE |
| oleoyl | N-oleoyl PE |
| linoleoyl | N-linoleoyl PE |
| elaidoyl | N-elaidoyl PE |

Example 14

Preparation of N-palmitoyl-phosphatidylethanolamine

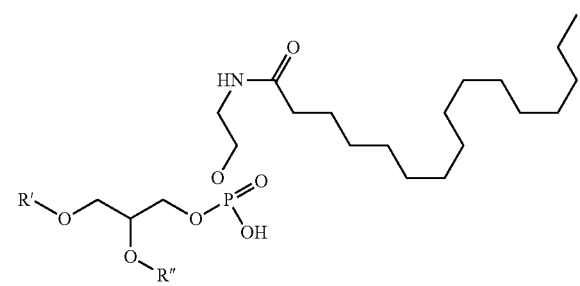

R' = acyl mixture, major component is palmitoyl
R" = acyl mixture, major component is oleoyl N-palmitoyl-phosphatidylethanolamine was prepared by the procedure described in Example 13. $^1$H NMR (600 MHz, Methanol-d4) δ 5.50-5.32 (m, 2H), 5.27 (quintet, J=5.5 Hz, 1H), 4.46 (dd, J=12.0, 3.1 Hz, 1H), 4.20 (dd, J=12.1, 6.9 Hz, 1H), 4.12 (ddd, J=9.5, 6.2, 3.5 Hz, 2H), 4.08-4.01 (m, 2H), 3.26-3.21 (m, 2H), 2.40-2.37 (t, J=7.7 Hz, 2H), 2.34 (t, J=7.7 Hz, 2H), 2.28 (t, J=7.5 Hz, 2H), 2.13-2.00 (m, 4H), 1.62 (m, 6H), 1.31 (m, 82H), 0.92 (t, J=6.9 Hz, 9H). Signals of the minor fatty acid derivatives: 5.50-5.32 (m, 2H), 2.90-2.77 (m, 3H)

$^{13}$C NMR (151 MHz, Methanol-d4) δ 173.48, 173.14, 172.95, 129.51, 129.31, 70.36, 63.51, 61.51, 60.86, 40.24, 33.53, 31.67, 29.5-28.8 (multiple signals), 24.85, 24.63, 22.33, 13.03.

Example 15

Preparation of N-decanoyl-phosphatidylethanolamine

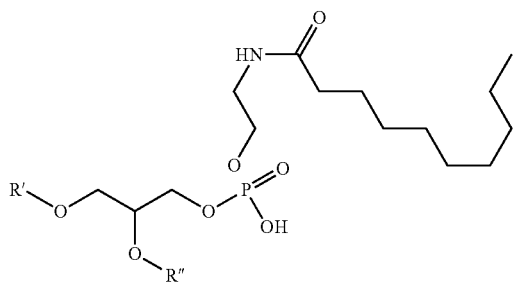

R' = acyl mixture, major component is palmitoyl
R" = acyl mixture, major component is oleoyl N-decanoyl-phosphatidylethanolamine was prepared by the procedure described in Example 13.

Example 16

Preparation of N-oleoyl-phosphatidylethanolamine

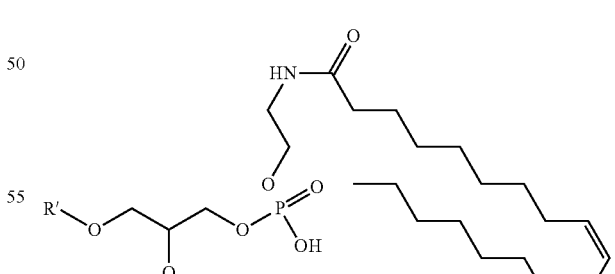

R' = acyl mixture, major component is palmitoyl
R" = acyl mixture, major component is oleoyl N-oleoyl-phosphatidylethanolamine was prepared by the procedure described in Example 13.

Example 17

Preparation of N-linoleoyl-phosphatidylethanolamine

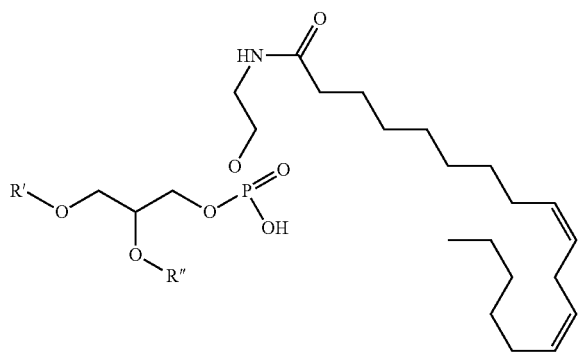

R' = acyl mixture, major component is palmitoyl
R″ = acyl mixture, major component is oleoyl N-linoleoyl-phosphatidylethanolamine was prepared by the procedure described in Example 13.

Example 18

Preparation of N-elaidoyl-phosphatidylethanolamine

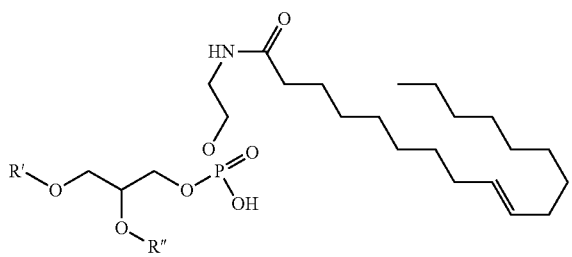

R' = acyl mixture, major component is palmitoyl
R″ = acyl mixture, major component is oleoyl N-elaidoyl-phosphatidylethanolamine was prepared by the procedure described in Example 13.

Example 19

Preparation of 1-acyl-lysophospholipids derived from N-palmitoyl PE, N-decanoyl PE, N-oleoyl PE, N-linoleoyl PE and N-elaidoyl PE, in a mixture with free (cleaved) fatty acid N-acyl phospholipid at 10% (w/v) concentration was repeatedly vortexed and sonicated at 43° C. in 50 mM Tris-HCl (pH 8.0, 50 mM KCl, 8 mM $CaCl_2$) until the phospholipid was completely dispergated, and then it was processed as described in Example 4—digested by phospholipase A2 at a ratio of 2 units of enzyme/mg phospholipid at 43° C. and the reaction was monitored by silica gel thin layer chromatography (TLC), eluted with chloroform:methanol:water 20:10:1. After complete cleavage, the reaction was stopped by the addition of EDTA to a concentration of 10 mM and stored at 0-4° C. The resulting products were labeled as shown in the following table:

| R2 | Designation of the product |
| --- | --- |
| palmitoyl | N-palmitoyl PE/E-DAPL + FA |
| decanoyl | N-decanoyl PE/E-DAPL + FA |
| oleoyl | N-oleoyl PE/E-DAPL + FA |
| linoleoyl | N-linoleoyl PE/E-DAPL + FA |
| elaidoyl | N-elaidoyl PE/E-DAPL + FA |

Example 20

Removal of Free Fatty Acids (FA) from the Products

The 1-acyl-lysophospholipid products prepared according to the present examples by enzymatic deacylation at sn-2 position to form a mixture with fatty acids (i.e., PE/E-DAPL+FA, PC/E-DAPL+FA and E-DAPL+FA, sn-1 hexanoyl PC/E-DAPL+FA, sn-1 stearoyl PC/E-DAPL+FA, sn-1 trimethylhexanoyl PC/E-DAPL+FA, sn-1 cyclopentanepropionyl PC/E-DAPL+FA, N-palmitoyl PE/E-DAPL+FA, N-decanoyl PE/E-DAPL+FA, N-oleoyl PE/E-DAPL+FA, N-linoleoyl PE/E-DAPL+FA, N-elaidoyl PE/E-DAPL+FA) were dissolved in ethanol, and then water and chloroform were gradually added to give an ethanol:water:chloroform ratio of 3:2:4. The mixture was shaken vigorously for 10 min, centrifuged for 5 min at 3000×g at room temperature, and the chloroform phase was isolated and evaporated. The residue was washed with n-hexane at 0-4° C. Insoluble lysophospholipids were obtained by centrifugation and the sediment was washed 3 times with n-hexane:acetone 1:2 (4° C.) and dried. The dried formulations were practically free of fatty acids and were designated PE/E-DAPL, PC/E-DAPL, E-DAPL, sn-1 hexanoyl PC/E-DAPL, sn-1 stearoyl PC/E-DAPL, sn-1 trimethylhexanoyl PC/E-DAPL, sn-1 cyclopentanepropionyl PC/E-DAPL, N-palmitoyl PE/E-DAPL, N-decanoyl PE/E-DAPL, N-oleoyl PE/E-DAPL, N-linoleoyl PE/E-DAPL and N-elaidoyl PE/E-DAPL.

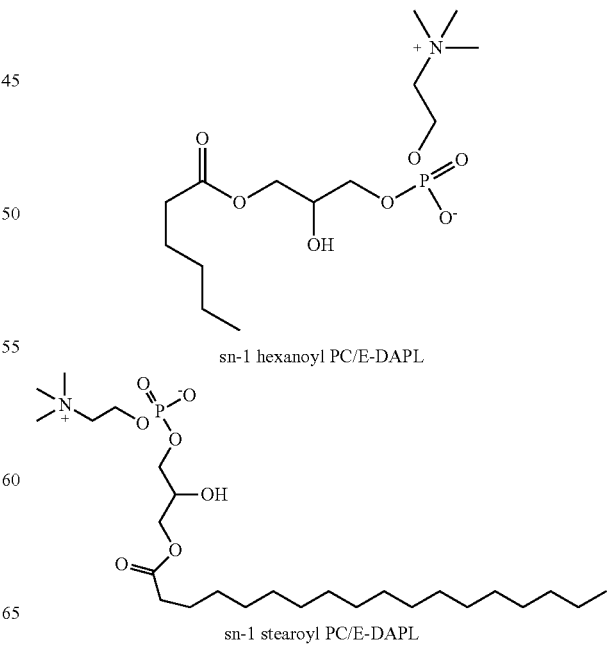

sn-1 hexanoyl PC/E-DAPL sn-1 stearoyl PC/E-DAPL

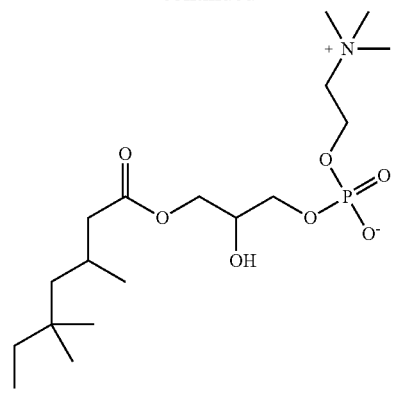

sn-1trimethylhexanoyl PC/E-DAPL

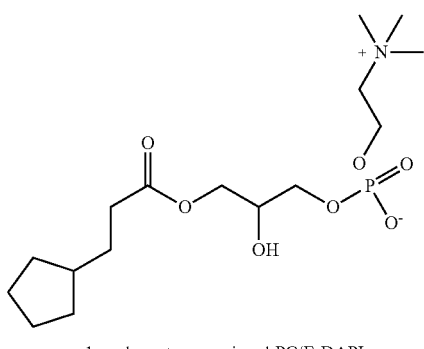

sn-1 cyclopentanepropionyl PC/E-DAPL

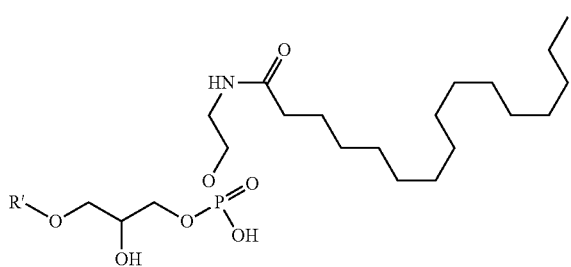

N-palmitoyl PE/E-DAPL
R' = acyl mixture, major component is palmitoyl

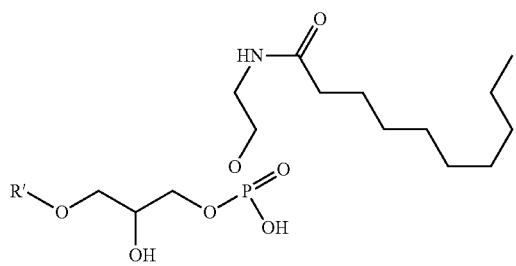

N-decanoyl PE/E-DAPL
R' = acyl mixture, major component is palmitoyl

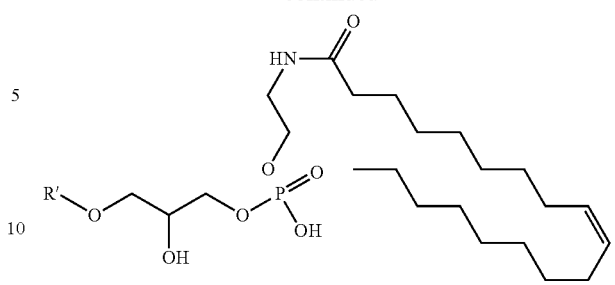

N-oleoyl PE/E-DAPL
R' = acyl mixture, major component is palmitoyl

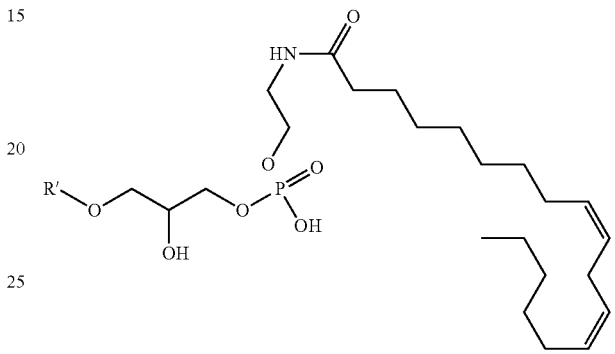

N-linoleoyl PE/E-DAPL
R' = acyl mixture, major component is palmitoyl

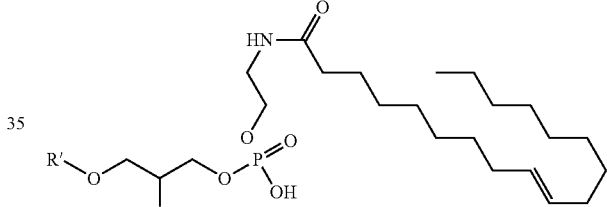

N-elaidoyl PE/E-DAPL
R' = acyl mixture, major component is palmitoyl

N-Palmitoyl PE/E-DAPL

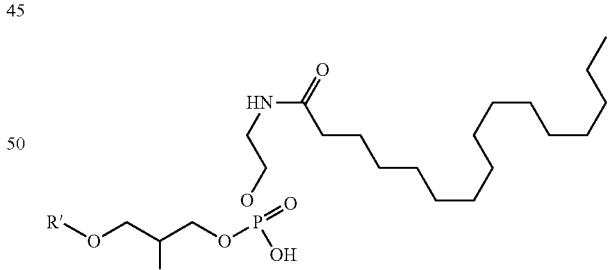

R' = acyl mixture, major component is palmitoyl $^1$H NMR (600 MHz, Methanol-d4) δ 4.19 (dd, J=11.4, 4.3 Hz, 1H), 4.13 (dd, J=11.3, 6.2 Hz, 1H), 4.08 (ddd, J=9.5, 6.2, 3.5 Hz, 2H), 4.02-3.97 (m, 1H), 3.95-3.88 (m, 2H), 3.19-3.15 (m, 2H), 2.37 (t, J=7.5 Hz, 4H), 2.37-2.15 (m, 2H), 1.63 (q, J=7.3 Hz, 4H), 1.31 (s, 52H), 0.92 (t, J=7.0 Hz, 2H).

$^{13}$C NMR (151 MHz, Methanol-d4) δ 174.13, 173.95, 2×130.05, 68.39, 66.41, 64.87, 61.62, 40.28, 33.50, 31.66, 29.62-28.69 (multiple signals), 24.60, 22.32, 12.96

Example 21

Effect of the Prepared Compounds and Mixtures on the Growth of Tumor Cells in Cell Culture This example demonstrates the effect of the prepared compounds and mixtures, i.e. PE/E-DAPL+FA, PC/E-DAPL+FA and E-DAPL+FA, sn-1 hexanoyl PC/E-DAPL+FA, sn-1 stearoyl PC/E-DAPL+FA, sn-1 trimethylhexanoyl PC/E-DAPL+FA, sn-1 cyclopentanepropionyl PC/E-DAPL+FA, N-palmitoyl PE/E-DAPL+FA, N-decanoyl PE/E-DAPL+FA, N-oleoyl PE/E-DAPL+FA, N-linoleoyl PE/E-DAPL+FA, N-elaidoyl PE/E-DAPL+FA and PE/E-DAPL, PC/E-DAPL, E-DAPL, sn-1 hexanoyl PC/E-DAPL, sn-1 stearoyl PC/E-DAPL, sn-1 trimethylhexanoyl PC/E-DAPL, sn-1 cyclopentanepropionyl PC/E-DAPL, N-palmitoyl PE/E-DAPL, N-decanoyl PE/E-DAPL, N-oleoyl PE/E-DAPL, N-linoleoyl PE/E-DAPL and N-elaidoyl PE/E-DAPL, on tumor cell growth in tissue culture. As a control, the starting phospholipids were used at the same concentrations and conditions. The starting phospholipids were PE, PC, sn-1 stearoyl PC, N-palmitoyl PE or the initial mixture of phospholipids, respectively.

The cytotoxic activity of the products was tested in tumor cell cultures C32 (human melanoma), TIB-75 (inducing murine hepatocarcinoma), LMH (chicken hepatocarcinoma).

A) C32 cells were cultured in D-MEM medium containing 10% fetal serum and penicillin+streptomycin at 37° C. in air/5% $CO_2$ atmosphere saturated with water vapor. Each well contained $5\times10^4$ cells and 0.5 ml medium. The tested products were added to the cells at concentrations of 0, 2.5, 5, 10, 20, 40, 80, 160 and 240 µM. After 16 hours of culture, cell state was recorded.

B) LMH cells were cultured in D-MEM medium containing 10% fetal serum and penicillin+streptomycin at 37° C. in air/5% $CO_2$ atmosphere saturated with water vapor. Each well contained $5\times10^4$ cells and 0.5 ml medium. The tested phospholipids were added to the cells at concentrations of 0, 2.5, 5, 10, 20, 40, 80, 160 and 240 µM. After 16 hours of culture, cell state was recorded.

C) TIB-75 cells were cultured in D-MEM medium containing 10% fetal serum and penicillin+streptomycin at 37° C. in air/5% $CO_2$ atmosphere saturated with water vapor. Each well contained $5\times10^4$ cells and 0.5 ml medium. The tested phospholipids were added to the cells at concentrations of 0, 2.5, 5, 10, 20, 40, 80, 160 and 240 µM. After 16 hours of culture, cell state was recorded.

The presence of free fatty acids did not have any significant effect on the toxicity of the products to the tested tumor cells.

The controls—PE, PC, sn-1 stearoyl PC, N-palmitoyl PE or the initial mixture of phospholipids—at exactly the same concentrations did not affect the phenotype or reduce the rate of cell growth. For comparison, 2-acyl-lysophospholipids prepared from PC, PE and total phospholipids were tested—these products were slightly cytotoxic, they needed about 4-5 times higher concentration to achieve the same level of toxicity as PE/E-DAPL, PC/E-DAPL, E-DAPL and sn-1 stearoyl PC/E-DAPL.

The cytotoxicity of the products was quantified by determining the ATP content in the cells and using neutral red intake, and the $IC50_{ATP}$ and $IC50_{NR}$ [µM] were determined. Both methods provided virtually the same values. The table shows $IC50_{ATP}$ values.

|  | C32 $IC50_{ATP}$ [µM] | LMH $IC50_{ATP}$ [µM] | TIB-75 $IC50_{ATP}$ [µM] |
|---|---|---|---|
| sn-1 stearoyl PC/E-DAPL | 45 | 40 | 45 |
| sn-1 hexanoyl PC/E-DAPL | 130 | 135 | 135 |
| sn-1 cyclopentanepropionyl PC/E-DAPL | 150 | 130 | |
| sn-1 trimethylhexanoyl PC/E-DAPL | 130 | 140 | |
| PC/E-DAPL | 50 | 35 | 45 |
| PE/E-DAPL | 35 | 30 | 35 |
| N-palmitoyl PE/E-DAPL | 150 | 140 | 140 |
| N-decanoyl PE/E-DAPL | 180 | | |
| N-oleoyl PE/E-DAPL | 180 | | |
| N-linoleoyl PE/E-DAPL | 180 | | |
| 2-acyl PC (15-20% 1-acyl PC) | 200 | | 210 |
| 2-acyl PE(15-20% 1-acyl PE) | 200 | | 200 |

Example 22

Effect of E-DAPL+FA on the Development of Experimental Hepatocarcinomas in Chickens 1-acyl-lysophosphatidyl derivatives E-DAPL+FA were administered perorally to chickens 5 times a week at 40 mg/20 g of chicken weight. Hepatocarcinomas were induced in the chickens in the embryonic stage by injection of LMH hepatocarcinoma cells. The experiment was evaluated on the 25th day from hatching of the chickens.

| Chickens | Number of chickens in the beginning of the experiment | Number of chickens surviving on the 25th day |
|---|---|---|
| infected, non-treated | 8 | 1 (multiple large hepatic carcinomas) |
| infected, treated by E-DAPL + FA | 8 | 4 (3 chickens were free of carcinomas, 1 chicken had 2 small hepatic carcinomas) |

Example 23

Effect of E-DAPL on the Development of Experimental Subcutaneous Tumors in Mice Subcutaneous tumors were induced in 16 BALB/c mice (8-10 weeks old) by injection of syngeneic TIB-75 cells. 8 mg of E-DAPL in 0.1 ml saline were administered once a week to a group of 8 mice, and 8 mg of control phospholipids (PLs) were administered once a week to a group of 8 mice, the administered products were applied to the developing tumor area. After 7 weeks, the tumors were dissected, their diameter was measured in three perpendicular directions, and the spherical volumes were calculated from the mean values. The mean volume of such approximated tumors in mice treated with E-DAPL was 30% of the volume of tumors in mice treated with control PLs.

Example 24

Effect of E-DAPL on the Development of Experimental Intraperitoneal Tumors in Mice Intraperitoneal tumors were induced in 20 BALB/c mice (8-10 weeks old) by injection of syngeneic TIB-75 cells. A control group of 10 mice was fed for eight weeks low-fat experimental food (Altromin) and a second group was fed the same diet containing 8 mg of E-DAPL per 5 g food. The mice received the experimental food 4 days a week; in the remaining 3 days they received standard food. Within 6 weeks of the start of the experiment, 2 control mice died of TIB-75 tumors. Then 2 equal groups of control and treated mice were dissected. The average tumor weight in the treated mice group was 75% of the weight of control tumors. After 2 more weeks the remaining mice were analyzed. The average tumor weight in the treated mice group was now 40% of the tumor weight in the control group. The experiment shows that E-DAPL administered in the diet (perorally) also slows down the growth of experimental intraperitoneal tumors.

Example 25

Effect of E-DAPL on the Development of Experimental Gastrointestinal (GIT) Tumors in Mice An experimental mouse model of familial adenomatous polyposis APC/Min was used to spontaneously produce premalignant polyps and eventually tumors in the small intestine of mice (LK Su, K W Kinzler, B. Vogelstein, A C Preisinger, A R Moser, C. Luongo, K A Gould, W F Dove: Multiple intestinal neoplasia caused by mutation in the murine homologue of the APC gene, Science 256 (1992), pp. 668-670)

E-DAPL was added to the mouse feed mixture—65 mg of E-DAPL/5 g of the low-fat diet. This amount was approximately consumed by every mouse every day. The mice were fed this modified feed mixture 3 days a week from 16 weeks of age (when they had many dozen polyps in the small intestine) until 28 weeks of age (when only the growing adenomas were present in the small intestine). The small intestine was isolated from the 28-week-old mice treated by E-DAPL and from the control mice fed unmodified low-fat diet 3 days a week, and processed to histological preparations. Evaluation of the preparations gave the following results (area rounded to 3 decimal places):

|  | E-DAPL | control | statistical significance/ p-value |
|---|---|---|---|
| average number of adenomas/mouse | 24.5 | 34.4 | 0.049062 |
| total area of adenomas [mm$^2$] | 2.975 | 11.741 | 0.026129 |
| average adenoma area [mm$^2$] | 0.121 | 0.337 | 0.005119 |

Conclusion: Long-term E-DAPL exposure does not adversely affect the physiology of experimental animals, and the administration of E-DAPL significantly inhibits the number and growth of adenomas (representative of GIT tumors) in the small intestine of APC/Min mice.

Example 26

Effect of E-DAPL on the Growth of Rapidly Growing Subcutaneous Transplanted Tumors Tumor growth in experimental BALB/C mice was induced by subcutaneous injection of syngeneic tumor cells CT26.CL25. Half of the mice were treated with E-DAPL. Two hundred microlitres of 0.3% E-DAPL (in saline containing 20% phosphate-buffered saline) were administered intravenously to every mouse 3 times per week. Control animals were similarly administered saline/20% phosphate-buffered saline. After three weeks, the tumors were harvested and weighed. The weight of the tumors from the treated animals was 42% of the weight of control tumors. The tumors in mice treated with E-DAPL were also of a limited type, even microscopically, in contrast to control tumors, which were markedly unbounded. This further confirms the beneficial effect of E-DAPL on reducing the growth of malignant tumors.

Conclusion: Intravenous administration of E-DAPL in saline is well tolerated and significantly inhibits the development of experimental tumors.

Conclusions drawn from in vivo experiments: Results of experiments given in examples 22-26 as well as additional in vivo experiments performed by the inventors revealed that peroral administration of an E-DAPL daily dose ranging from 400 to 3200 mg/kg of the animal's live weight had no observable adverse effect on experimental animals but inhibited growth of various experimental tumors. As a rule, higher doses were progressively more efficient. Intravenous administration of 0.3% E-DAPL solution was well tolerated by mice and proved to be an efficient way of inhibition of tumors, in particular tumors with well developed vascular supply.

Example 27

Synergic Effect of Co-Administration of E-DAPL and an Anticancer Drug Doxorubicin (Dox)

The potentiation of cytotoxic effect of E-DAPL/Dox combination was evaluated. The dose-effect relationship of individual drugs and E-DAPL/Dox mixture (ratio 202:1 was tested) was determined on mammary gland 4T1 cancer cell line by means of crystal violet assay (three measurements). The linearized Median-Effect Plot of dose response line provided both parameters (IC$_{50}$; trend line m value) of Median-Effect Equation for individual and combination treatment [ref: Theoretical basis, experimental design, and computerized simulation of synergism and antagonism in drug combination studies; Ting-Chao Chou: Pharmacol Rev. 58(3), 2006, 621-81; Erratum in Pharmacol Rev. 2007; 59(1), 124]:

Median-effect equation $$\left(\frac{f_a}{f_u}\right) = \left(\frac{D}{IC_{50}}\right)^m$$

Linearized Median-effect plot $$\log(f_a/f_u) = m \log(D) - m \log(IC_{50})$$

| Calculated parameters of the dose-effect relationship | | | |
|---|---|---|---|
| | Calculated from the Median-Effect Plot | | |
| | IC$_{50}$ [µM] | m value trend line] | Dose-effect curve |
| E-DAPL | 160.37 | 1.8886 | sigmoidal |
| Dox | 0.93 | 0.7877 | flat sigmoidal |
| E-DAPL/Dox (202:1) | 46.45 | 0.8904 | ~flat sigmoidal |

Potentiation of combination effect of E-DAPL/Dox/202:1 was expressed for the concentrations $IC_1$ to $IC_{60}$ by calculation of Combination index (CI) applying Combination Index Theorem for mutually nonexclusive drugs that obey higher order conditions [ref: Quantitative analysis of dose-effect relationships: the combined effects of multiple drugs or enzyme inhibitors; Ting-Chao Chou, Paul Talalay: Advances in Enzyme Regulation, Volume 22, 1984, Pages 27-55]:

$$CI = \frac{D_1}{(D_x)_1} + \frac{D_2}{(D_x)_2} + \frac{D_1 D_2}{(D_x)_1 (D_x)_2}$$

$CI < 1$ (synergism); $CI = 1$ (additive effect); $CI > 1$ (antagonism)

wherein:

$$D_x = (IC_{50})[f_a/(1-f_a)]^{\frac{1}{m}}$$

$$D_1 = (D_x)_{1,2} \times [1/(202+1)]$$

$$D_2 = (D_x)_{1,2} \times [202/(202+1)]$$

$D_1$-dose of first drug in mixture;

$D_2$-dose of second drug in mixture

| Combination index for $IC_1$ to $IC_{60}$ concentration range | | | | | |
|---|---|---|---|---|---|
| $IC_{1-20}$ | CI | $IC_{21-40}$ | CI | $IC_{41-60}$ | CI |
| $IC_1$ | 0.510 | $IC_{21}$ | 0.469 | $IC_{41}$ | 0.552 |
| $IC_2$ | 0.476 | $IC_{22}$ | 0.472 | $IC_{42}$ | 0.557 |
| $IC_3$ | 0.461 | $IC_{23}$ | 0.475 | $IC_{43}$ | 0.563 |
| $IC_4$ | 0.452 | $IC_{24}$ | 0.479 | $IC_{44}$ | 0.568 |
| $IC_5$ | 0.448 | $IC_{25}$ | 0.482 | $IC_{45}$ | 0.574 |
| $IC_6$ | 0.445 | $IC_{26}$ | 0.486 | $IC_{46}$ | 0.580 |
| $IC_7$ | 0.443 | $IC_{27}$ | 0.490 | $IC_{47}$ | 0.586 |
| $IC_8$ | 0.443 | $IC_{28}$ | 0.493 | $IC_{48}$ | 0.592 |
| $IC_9$ | 0.443 | $IC_{29}$ | 0.497 | $IC_{49}$ | 0.598 |
| $IC_{10}$ | 0.444 | $IC_{30}$ | 0.501 | $IC_{50}$ | 0.605 |
| $IC_{11}$ | 0.445 | $IC_{31}$ | 0.505 | $IC_{51}$ | 0.612 |
| $IC_{12}$ | 0.447 | $IC_{32}$ | 0.509 | $IC_{52}$ | 0.619 |
| $IC_{13}$ | 0.448 | $IC_{33}$ | 0.514 | $IC_{53}$ | 0.626 |
| $IC_{14}$ | 0.450 | $IC_{34}$ | 0.518 | $IC_{54}$ | 0.633 |
| $IC_{15}$ | 0.453 | $IC_{35}$ | 0.523 | $IC_{55}$ | 0.641 |
| $IC_{16}$ | 0.455 | $IC_{36}$ | 0.527 | $IC_{56}$ | 0.649 |
| $IC_{17}$ | 0.457 | $IC_{37}$ | 0.532 | $IC_{57}$ | 0.657 |
| $IC_{18}$ | 0.460 | $IC_{38}$ | 0.537 | $IC_{58}$ | 0.665 |
| $IC_{19}$ | 0.463 | $IC_{39}$ | 0.542 | $IC_{59}$ | 0.674 |
| $IC_{20}$ | 0.466 | $IC_{40}$ | 0.547 | $IC_{60}$ | 0.683 |

Data shown in the table above indicate synergy of E-DAPL and Dox. Synergy of both drugs is more pronounced at lower concentrations. The abovementioned data indicate significant potentiation of effect of an established anticancer agent Dox when combined with E-DAPL. For example, concentration of Dox at $IC_{25}$Dox and $IC_{25}$E-DAPL/Dox/202:1 for 4T1 cell line is 0.2306 μM and 0.066 μM respectively. This allows for 71% dose reduction of cardio toxic Dox without diminishing the $IC_{25}$ cytotoxic effect. For $IC_{50}$ level is the relative dose reduction 0.9303 μM vs 0.2287 μM (75%). Calculation of Combination index by less accurate method for mutually exclusive drugs afforded even more favorable values of CI [ref: Quantitative analysis of dose-effect relationships: the combined effects of multiple drugs or enzyme inhibitors; Ting-Chao Chou, Paul Talalay: Advances in Enzyme Regulation, Volume 22, 1984, Pages 27-55].

The invention claimed is:

1. A method of treating cancer consisting of administering at least one 1-acyl-lysophosphatidyl derivative to a patient in need thereof, wherein the at least one 1-acyl-lysophosphatidyl derivative is of general formula I

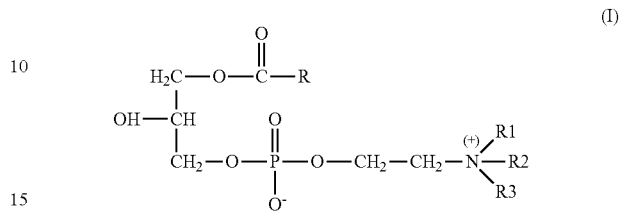

wherein:

R is a C13 to C30 linear or branched alkyl,

R1 is selected from the group consisting of H and C1 to C10 alkyl,

R2 is selected from the group consisting of H, C10 to C30 acyl and C1 to C10 alkyl, and R3, when present, is selected from the group consisting of H and C1 to C10 alkyl, wherein the cancer is selected from the group consisting of a hepatocarcinoma and a melanoma.

2. A method of treating cancer consisting of administering at least one 1-acyl-lysophosphatidyl derivative and at least one anticancer drug to a patient in need thereof, wherein the at least one 1-acyl-lysophosphatidyl derivative is of general formula I

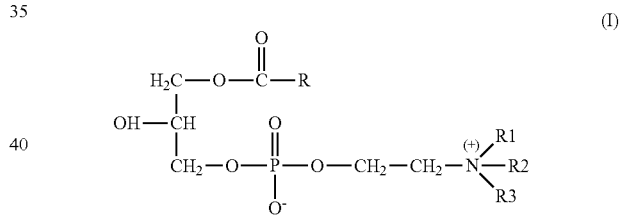

wherein:

R is a C13 to C30 linear or branched alkyl,

R1 is selected from the group consisting of H and C1 to C10 alkyl,

R2 is selected from the group consisting of H, C10 to C30 acyl and C1 to C10 alkyl, and R3, when present, is selected from the group consisting of H and C1 to C10 alkyl, wherein the at least one 1-acyl-lysophosphatidyl derivative and the at least one anticancer drug are administered in a ratio of at least 100:1 in separate formulations, wherein the cancer is selected from the group consisting of a hepatocarcinoma and a melanoma.

3. The method of claim 2, wherein the ratio is at least 180:1.

4. The method of claim 2, wherein the ratio is at least 200:1.

5. The method of claim 2, wherein the 1-acyl-lysophosphatidyl derivative and the anticancer drug are administered within 12 hours of each other.

6. The method of claim 2, wherein the 1-acyl-lysophosphatidyl derivative and the anticancer drug are administered within 6 hours of each other.

7. The method of claim 2, wherein the 1-acyl-lysophosphatidyl derivative and the anticancer drug are administered within 6 hours of each other.

8. The method of claim 1, wherein R is C13 to C30 linear alkyl.

9. The method of claim 1, wherein R is C13 to C20 linear or branched alkyl.

10. The method of claim 1, wherein R is C13 to C20 linear alkyl.

11. The method of claim 2, wherein R is C13 to C30 linear alkyl.

12. The method of claim 2, wherein R is C13 to C20 linear or branched alkyl.

13. The method of claim 2, wherein R is C13 to C20 linear alkyl.

14. The method of claim 2, wherein the anticancer drug is doxorubicin.

\* \* \* \* \*